United States Patent [19]

Reinehr et al.

[11] Patent Number: 4,663,365
[45] Date of Patent: May 5, 1987

[54] WASH-RESISTANT, ANTIMICROBIALLY-ACTIVE FIBRES AND THREADS AND THEIR MANUFACTURE

[75] Inventors: Ulrich Reinehr, Dormagen; Klaus Sasse, Bergisch Gladbach; Gerhard Jäger, Leverkusen; Walter Radt, Krefeld, all of Fed. Rep. of Germany

[73] Assignee: Bayer Aktiengesellschaft, Leverkusen, Fed. Rep. of Germany

[21] Appl. No.: 762,652

[22] Filed: Aug. 5, 1985

[30] Foreign Application Priority Data

Aug. 18, 1984 [DE] Fed. Rep. of Germany ...... 3430511

[51] Int. Cl.⁴ ............................................. D01F 1/10
[52] U.S. Cl. .................................. 523/122; 8/115.59; 8/510; 264/176.1; 264/182; 524/565
[58] Field of Search ........................ 523/122; 524/565; 264/176 F, 182; 8/510, 115.59; 428/907, 361, 375, 394

[56] References Cited

U.S. PATENT DOCUMENTS

| | | | |
|---|---|---|---|
| 3,096,183 | 7/1963 | Genth | 523/122 |
| 3,154,511 | 10/1964 | Logemann et al. | 524/565 |
| 3,198,765 | 8/1965 | Lowes | 523/122 |
| 3,232,904 | 2/1966 | Seibert et al. | 524/565 |
| 3,959,556 | 5/1976 | Morrison | 428/907 |
| 4,111,879 | 9/1978 | Mori et al. | 428/907 |
| 4,343,853 | 8/1982 | Morrison | 428/907 |
| 4,401,712 | 8/1983 | Morrison | 428/289 |

Primary Examiner—Ronald W. Griffin
Attorney, Agent, or Firm—Sprung Horn Kramer & Woods

[57] ABSTRACT

Threads and fibres of synthetic polymers containing from 0.1 to 5% by weight, based on the polymer, of one or more than one compound corresponding to the formula (I)

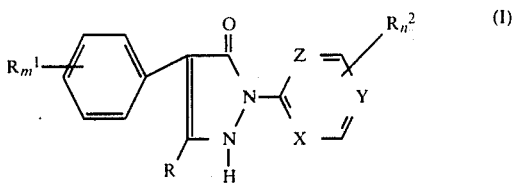

wherein
R represents hydrogen or alkyl,
$R^1$ represents halogen, hydroxyl, optionally substituted alkyl, optionally substituted alkoxy, optionally substituted phenoxy, a group $-S(O)_p$-alkyl which is optionally substituted in the alkyl portion, nitro, optionally substituted amino or a condensed carbocyclic or heterocyclic group,
p stands for the numerical value 0, 1 or 2,
$R^2$ represents halogen, alkyl which is optionally substituted, alkoxy, alkylmercapto, nitro, cyano, carboxylic acid amide or a condensed carbocyclic group,
m represents an integer from 0 to 5,
n represents an integer from 0 to 4, the substituents being either identical or different when m and/or n has a value greater than 1, and X, Y and Z are identical or different and represent a nitrogen atom, the group =CH— or

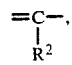

where $R^2$ has the meaning indicated above, with the proviso that at least one of the substituents, X, Y and Z is a nitrogen atom, manifest antimicrobial activity which persists even after dyeing and washing processes.

9 Claims, No Drawings

WASH-RESISTANT, ANTIMICROBIALLY-ACTIVE FIBRES AND THREADS AND THEIR MANUFACTURE

This invention relates to wash-resistant, antimicrobially active fibres, threads and filament yarns and to a process for their manufacture.

The term "antimicrobially finished fibres" is used to denote fibres which manifest both antibacterial and antimycotic activity as a result of the addition of chemically active substances. The term "wash-resistant, antimicrobially active fibres" is used to denote fibres whose antimicrobial activity persists even after a dyeing process and several washing processes.

The antimicrobial finishing of fibres and textile structures is known. These finishing processes are generally subdivided into methods of application to the finished fibre and methods of application during production of the fibre. Methods of application to the finished fibre include, for example, the application of active chemical ingredients to piece goods, yarn and combed sliver by the extraction or padding process.

Methods known in the literature for application during production of the fibres include the introduction of antimicrobially-active substances, e.g. phosphorylated salicylic acid anilides, into the spinning solution of the polymer (DE-OS No. 2 220 907). This method achieves homogeneous distribution of the active substance over the whole cross-section of the fibre. Other processes described include the incorporation of active substances by copolymerisation (DE-OS No. 1 542 945), by microencapsulation (DE-OS No. 2 231 903) or by the introduction of an antimicrobial agent into a homogeneous melt of a fibre-forming polymer (DE-OS No. 3 214 610). Yet another process provides for the antimycotic finishing of synthetic fibres produced by the melt spinning process by linking active substances to the polymer by means of bonding agents before the polymer is formed into threads or filaments (DE-OS No. 2 710 469). All the different methods of applying the active ingredient to finished fibres and knitted textiles have the characteristic that, due to being applied after production of the fibres or textile goods, they have little wash resistance and rapidly lose their antimicrobial activity. If, on the other hand, the active ingredients are introduced into the spinning solution of the polymer, it is necessary to add them in large quantities to produce am antimicrobial effect, especially when a dry spinning process is employed. By far the greater proportion of the active ingredient is bound in an ineffective form in the interior of the polymer fibre and only the small proportion which reaches the surface of the fibre is antimicrobially-active. The use of high proportions of active ingredients in the spinning solution, however, has a very deleterious effect on important properties of the fibres. Thus the fibres are often observed to suffer a loss in strength, insufficient light fastness and colour fastness, streakiness of the dyed product, the formation of vacuoles and problems relating to the grey tone of the undyed product and the handle and gloss.

It is therefore an object of the present invention to provide antimicrobially-active synthetic fibres which do not have the disadvantages mentioned above and still manifest a high antimicrobial activity after dyeing and washing processes.

The present invention therefore relates to threads and fibres of synthetic polymers containing from 0.1 to 5% by weight, based on the polymer, of one or more than one compound corresponding to formula (I)

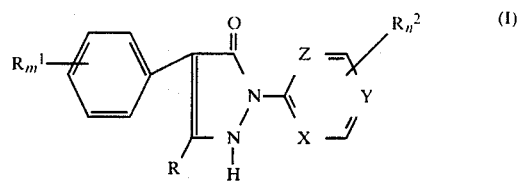

wherein
R represents hydrogen or alkyl,
R¹ represents halogen, hydroxyl, optionally substituted alkyl, optionally substituted alkoxy, optionally substituted phenoxy, a group —S(O)$_p$—alkyl which is optionally substituted in the alkyl portion, nitro, optionally substituted amino or a condensed carbocyclic or heterocyclic group,
p stands for the value 0 or the integer 1 or 2,
R² represents halogen, alkyl which is optionally substituted alkoxy, alkylmercapto, nitro, cyano, carboxylic acid amide or a condensed carbocyclic group,
m represents an integer from 0 to 5,
n represents an integer from 0 to 4, and the substituents may be identical or different when m and/or n has a value greater than 1, and
X, Y and Z may be identical or different and represent a nitrogen atom or the group =CH— or

where R²
has the meaning indicated above, with the proviso that at least one of the substituents, X, Y, Z is a nitrogen atom.

The threads and fibres may in particular be polyacrylonitrile threads and fibres containing at least 45% by weight of acrylonitrile units. The acrylonitrile polymers used may be any acrylonitrile homopolymers or copolymers capable of being spun into so-called acrylic fibres or modacrylic fibres, preferably acrylonitrile copolymers containing at least 85% by weight of acrylonitrile units.

The antimicrobially-active threads and fibres are obtained by introducing one or more compounds corresponding to formula I in a quantity of from 0.1 to 5% by weight, based on the polymer, into a spinning solution of the polymer, preferably a polyacrylonitrile spinning solution, spinning the solution to threads by the dry spinning process, after-treating them by washing, stretching, dressing, drying, crimping and cutting into fibres, and finally subjecting the product to a process of fixing with saturated steam at a temperature of at least 120° C. for at least 3 minutes. By employing this fixing process it is surprisingly found that a high antimicrobial activity which is resistant to dyeing and washing can be obtained. Spinning tests have shown that even when large quantities of antimicrobial agent were added to the spinning solution, for example, 5% by weight of compounds of formula I (see Examples 5 and 6) it was not possible to obtain an antimicrobial effect unless fixing by saturated steam was carried out. Other attempts to obtain an antimicrobial finish on fibres produced by the dry spinning process by carrying out various aqueous treatments at boiling point under reflux, under conditions of dyeing at various pH values (see Table 6) or by means of short steam treatments and at lower temperatures (see Table 5), were not successful.

The fixing process is preferably carried out for 3 to 15 minutes at 120° to 150° C.

The active ingredients used must be soluble in the spinning solvent, e.g. dimethylformamide, to ensure that a homogeneous spinning solution with even distribution of the active ingredient will be obtained. At the same time, they should be substantially insoluble in water so that they will not be washed out during subsequent treatment of the fibres. Furthermore, the active ingredients must not be steam volatile in order that they may not be lost during the fixing process. Lastly, the active ingredients must not have a deleterious effect on important properties of the fibres, such as their gloss, handle and dye absorption capacity.

The compounds of formula (I) may exist in tautomeric equilibrium with the compounds of formula (IA):

m represents an integer from 0 to 3, n represents an integer from 0 to 3, and the substituents may be identical or different when m and/or n has a value greater than 1, and X, Y and Z, which may be identical or different, represent a nitrogen atom or the group =CH— or

where $R^2$ has the meaning indicated above, with the proviso that one or two of the groups X, Y, Z is a nitrogen atom.

Particularly preferred are those compounds corresponding to formula (I) in which R represents hydrogen, methyl or ethyl, $R^1$ represents fluorine, chlorine, bromine, methyl, ethyl, trifluoromethyl, methoxy, ethoxy, trifluoromethoxy, phenoxy, methylthio, ethylthio,

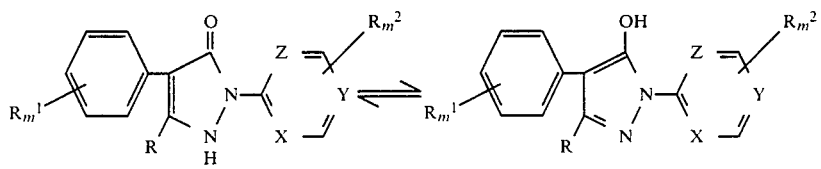

I       IA

For the sake of simplicity, however, the text will refer hereinafter only to compounds of formula (I) although this term is intended to include both the pure compounds and mixtures containing varying proportions of compounds of the formulae (I) and (IA).

The compounds of formula I are prepared from α-acylphenylacetic acid esters or derivatives thereof and heretocyclic hydrazine compounds, optionally in the presence of an acid or base.

Those compounds corresponding to formula (I) are preferred in which

R represents hydrogen, methyl, or ethyl, $R^1$ represents fluorine, chlorine, bromine, methyl, ethyl, n-propyl, isopropyl, trifluoromethyl, dichlorofluoromethyl, methoxy, ethoxy, n-propoxy, iso-propoxy, trifluoromethoxy, dichlorofluoromethoxy, methylthiomethoxy, ethylthiomethoxy, 1-methylthio-ethoxy, 2-ethylthio-ethoxy, phenoxymethoxy, phenoxy, methylthio, ethylthio, trifluoromethylthio, dichlorofluoromethylthio, methoxymethylthio, ethoxymethylthio, methylthiomethylthio, methylsulphinyl, ethylsulphinyl, methylsulphonyl, nitro, cyano, amino, methylamino, ethylamino, dimethylamino, diethylamino, a condensed benzene ring or a condensed 5- or 6-membered heterocyclic ring which contains one or two oxygen atoms and may be monosubstituted or polysubstituted with fluorine, $R^2$ represents fluorine, chlorine, bromine, methyl, ethyl, n-propyl, isopropyl, tert.-butyl, trifluoromethyl, dichlorofluoromethyl, methoxymethyl, ethoxymethyl, methylthiomethyl, methoxy, ethoxy, n-propoxy, isopropoxy, methylthio, ethylthio, nitro, cyano, aminocarbonyl or a condensed benzene ring, trifluoromethylthio, nitro, cyano, amino, dimethylamino, a condensed benzene ring or a condensed, 5-membered heterocyclic ring which has two oxygen atoms and is substituted with several fluorine atoms, $R^2$ represents fluorine, chlorine, bromine, methyl, ethyl, tert.-butyl, trifluoromethyl, methoxy, methylthio, nitro, cyano, aminocarbonyl or a condensed benzene ring, m represents an integer from 0 to 3, n represents an integer from 0 to 3, and either X represents a nitrogen atom and Y and Z represents the group =CH— or

or

Y represents a nitrogen atom and

X and Z represents the group =CH— or

or

X and Z each represent a nitrogen atom and

Y represents the group =CH— or

or

X and Y each represent a nitrogen atom and

Z represents the group =CH— or

The compounds corresponding to formula I are preferably used in a quantity of from 0.5 to 1% by weight, based on the polymer solids content.

The fibres according to the invention can be further processed to textiles in the textile industry under the usual conditions. For these processes, the pure fibres may be used or they may be mixed with fibres which do not have an antimicrobial finish. Textiles for which antimicrobial finishing is particularly desirable are products such as carpets, furnishing fabrics, bath mats, curtains, tents, tarpaulins, cushions and awnings.

Determination of the antimicrobial activity

Microbiological tests in the form of the agar diffusion test against three different test microorganisms were carried out on the fibres and knitted goods which had been treated with the antimicrobial finish according to the invention.

Agar diffusion test:

1 g each of the antimicrobially finished, first undyed and then dyed fibres and knitted samples measuring 2×2 cm, unwashed and after 10 washings, were placed in Petri dishes with Nervina agar (composition: 60 g Nervina malt, 5 g NaCl, 5 g peptone, 5 g glycerol made up to 1 l of water) so that they were completely covered with nutrient substrate. The surfaces of these prepared Petri dishes were then homogeneously inoculated with suspensions of mould fungi or bacteria. Those which were inoculated with mould fungi were incubated for 7 days at 30° C. and those inoculated with bacteria were incubated for 3 days at 37° C. The mould fungi used were spore suspensions of Aspergillus fumigatus and Chaetomium globosum.

The bacteria used as test microorganisms were Staphylococcus aureus in the form of Standard I nutrient agar (Merck No. 1621). The expected zones of growth inhibition were then measured and assessed as follows:

Grade 1: No reduction in growth on the test sample.
Grade 2: Growth covering up to 25% of the surface of the sample
Grade 3: Test sample free from growth
Grade 4: Test sample free, halo of inhibition up to 2 mm
Grade 5: Test sample free, halo of inhibition over 2 mm.

All tests were duplicated, including the growth and nutrient media controls.

The following Examples serve to explain the invention in more detail. All percentages given are based on weight unless otherwise indicated.

EXAMPLE 1

An acrylonitrile copolymer of 93.6% acrylonitrile, 5.7% methyl acrylate and 0.7% sodium methallylsulphonate, K-value 81, was converted into a spinning solution with 30% solids content by dissolving with dimethylformamide with stirring and one hour's heating at 80° C. with the addition of 0.1% of 1-pyridyl-(2)-4-phenylpyrazolin-5-one, based on the polymer solids content.

The spinning solution was then filtered and spun by the dry spinning method from a 240-aperture spinning die at a draw-off rate of 350 m/min. The spun material, which had a total titre of 2280 dtex, was collected on bobbins and gathered together to form an after-treatment cord having a total titre of 1,140,000 detex. This cable was washed in water at 80° C. and then stretched by 1:3.6 in boiling water. The cable was then treated with an antistatic dressing and dried in a tumbler drier at 160° C. under conditions allowing for 20% shrinkage. The cable was then crimped, cut up into staple fibres 60 mm in length and fixed with saturated steam at 120° C. in a screen belt steamer for 5 minutes. The proportion of fibres put through the process to the quantity of saturated steam was 1 to 1. The staple fibres were then air blasted and conveyed to a bale press. The final individual fibre titre was 3.3 dtex. A proportion of the antimicrobially finished fibres was then dyed with a blue dye corresponding to the formula

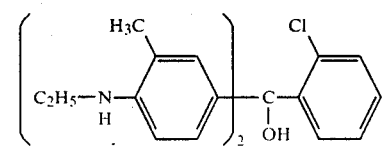

Both the undyed and the blue dyed, antimicrobially finished fibres were then spun to form three-cylinder yarns with dtex 276×1 (Nm 36/1) which were used to produce knitted goods in a Milanese ribbed pattern. The knitted samples were then subjected 10 times to a domestic wash at a temperature of 30° C. for the pre-wash and main wash and a liquor ratio of 1:30, using 5 g/l of commercial detergent recommended for use at 30° C. The goods were rinsed three times after each washing process, with intermediate drying at 60° C. in the tumbler direr. The microbiological tests in the form of the agar diffusion test carried out on fibres and knitted pieces are summarized in the Table below. The results were assessed according to the grading indicating earlier.

The letter a–d shown next to the sample in Table 1 have the following meaning:
a=untreated, undyed fibre or knitted piece
b=undyed fibre or knitted piece after 10 washings
c=dyed fibre or knitted piece
d=dyed fibre or knitted piece after 10 washings.

TABLE 1

| Sample | Treatment | Inhibition against mould fungi | | Bacteria Staphylococcus aureus |
| --- | --- | --- | --- | --- |
| | | Aspergillus fumigatus | Chaetomium globosum | |
| Fibre | a | 5 | 5 | 5 |
| | b | 4 | 4 | 5 |
| | c | 4 | 4 | 5 |
| | d | 3 | 3 | 3 |
| Knitted sample | a | 5 | 5 | 5 |
| | b | 4 | 4 | 4 |
| | c | 4 | 4 | 4 |
| | d | 3 | 3 | 3 |

EXAMPLE 2

An acrylonitrile copolymer according to Example 1 was dissolved as described there and converted into a spinning solution with the addition of 0.5% of 1-pyridyl-(2)-4-phenylpyrazolin-5-one. Spinning to threads and after-treatment to form fibres with an individual end titre of 3.3 dtex were carried out as described in Example 1. A proportion of the fibres was again dyed blue and both the undyed and dyed fibres were made up into knitted pieces and subjected to 10 household washes and then to a microbiological test. The results are shown in Table 2 below.

TABLE 2

| Sample | Treatment | Inhibition against mould fungi | | Bacteria |
|---|---|---|---|---|
| | | Aspergillus fumigatus | Chaetomium globosum | Staph. aureus |
| Fibres | a | 5 | 5 | 5 |
| and | b | 5 | 5 | 5 |
| knitted | c | 5 | 5 | 5 |
| pieces | d | 5 | 5 | 5 |

It is clear from Example 2 that an excellent antimicrobial activity is obtained for the antimicrobially finished fibres and knitted pieces in the undyed, dyed and repeatedly washed state.

EXAMPLE 3

An acrylonitrile copolymer according to Example 1 was dissolved as indicated there and converted into a spinning solution with the addition of 0.1% of 1-pyrimidyl-(2)-4-phenylpyrazolin-5-one. Spinning of the solution into threads and their subsequent after-treatment to form fibres with a final titre of 3.3 dtex were carried out as in Example 1. A proportion of the fibres was again dyed blue and the undyed and dyed fibres were made up into knitted pieces and subjected to 10 household washings and then tested microbiologically. The results are shown in Table 3.

TABLE 3

| Sample | Treatment | Inhibition against mould fungi | | Bacteria |
|---|---|---|---|---|
| | | Aspergillus fumigatus | Chaetomium globosum | Staph. aureus |
| Fibre | a | 5 | 5 | 5 |
| | b | 4 | 4 | 4 |
| | c | 4 | 3 | 4 |
| | d | 3 | 3 | 3 |
| Knitted | a | 5 | 5 | 5 |
| piece | b | 4 | 3 | 4 |
| | c | 3 | 3 | 4 |
| | d | 3 | 3 | 3 |

EXAMPLE 4

An acrylonitrile copolymer according to Example 1 was dissolved as described there and converted into a spinning solution with the addition of 0.5% of 1-pyrimidyl-(2)-4-phenylpyrazolin-5-one.

Spinning into threads and subsequent after-treatment to form fibres with an individual titre of 3.3 dtex were carried out as indicated in Example 1. A proportion of the fibres was again dyed blue and the dyed and undyed fibres were made up into knitted pieces which were subjected to 10 household washings and then tested microbiologically. The results are shown in Table 4.

TABLE 4

| Sample | Treatment | Inhibition against mould fungi | | Bacteria |
|---|---|---|---|---|
| | | Aspergillus fumigatus | Chaetomium globosum | Staph. aureus |
| Fibres | a | 5 | 5 | 5 |
| and | b | 5 | 5 | 5 |
| knitted | c | 5 | 5 | 5 |
| pieces | d | 5 | 5 | 5 |

Table 5 below shows the antimicrobial activity of fibres which have been produced as in Examples 2 and 4 but with different steam treatments.

Table 6 shows the antimicrobial activity obtained for fibres which have been produced according to Examples 2 and 4 but given various aqueous treatments without the steam treatment. Blank dyeing was carried out at boiling point at a pH of 4 to 5. The dyeing experiments were carried out as follows: 5 g of fibres which had been scratched open were boiled under reflux with 1 l of dye bath in a flask for one hour and two hours, respectively. Dye was still present in excess after the dyeing process. The dyed fibres were then washed under running water, boiled in water for 30 minutes and dried at 50° C. The dye bath contained 1 g/l of the blue dye of 0.2 g/l Avolan IW and 1 g/l of sodium acetate. The dye bath was adjusted to a pH of about 4 with about 0.2 to 0.5 ml/l of glacial acetic acid.

TABLE 5

| No. | Sample | Steamer temperature °C. | Steaming time min. | Inhibition against mould fungi | | Bacteria |
|---|---|---|---|---|---|---|
| | | | | Aspergillus fumigatus | Chaetomium globosum | Staph. aureus |
| 1 | Fibres according to Example 2 | 105 | 5 | 2 | 1-2 | 2 |
| 2 | Fibres according to Example 2 | 110 | 5 | 2 | 2 | 2 |
| 3 | Fibres according to Example 2 | 120 | 3 | 3 | 3 | 3 |
| 4 | Fibres according to Example 2 | 120 | 4 | 4 | 4 | 5 |
| 5 | Fibres according to Example 2 | 130 | 3 | 5 | 5 | 5 |
| 6 | Fibres according to | 105 | 5 | 2 | 2 | 2 |

TABLE 5-continued

| No. | Sample | Steamer temperature °C. | Steaming time min. | Inhibition against mould fungi | | Bacteria Staph. aureus |
|---|---|---|---|---|---|---|
| | | | | *Aspergillus fumigatus* | *Chaetomium globosum* | |
| 7 | Fibres according to Example 4 | 110 | 5 | 2 | 2 | 3 |
| 8 | Fibres according to Example 4 | 120 | 3 | 3 | 3 | 4 |
| 9 | Fibres according to Example 4 | 120 | 4 | 5 | 4 | 5 |
| 10 | Fibres according to Example 4 | 130 | 3 | 5 | 5 | 5 |

TABLE 6

| No. | Sample | Type of aqueous treatment | Inhibition against mould fungi | | Bacteria Staph. aureus |
|---|---|---|---|---|---|
| | | | *Aspergillus fumigatus* | *Chaetomium globosum* | |
| 1 | Fibres according to Example 2 | Boiling water /1 hour | 1 | 1 | 1 |
| 2 | Fibres according to Example 2 | Boiling water /10 hour | 2 | 1-2 | 2 |
| 3 | Fibres according to Example 2 | Blank dyeing /1 hour | 1 | 1 | 1 |
| 4 | Fibres according to Example 2 | Blank dyeing /2 hours | 1 | 1-2 | 1 |
| 5 | Fibres according to Example 2 | Dyeing test /1 hour | 1 | 1 | 1 |
| 6 | Fibres according to Example 2 | Dyeing test /2 hours | 1-2 | 1 | 1-2 |
| 7 | Fibres according to Example 4 | Boiling water /1 hour | 1 | 1 | 1 |
| 8 | Fibres according to Example 4 | Boiling water /10 hours | 2 | 2 | 2 |
| 9 | Fibres according to Example 4 | Blank dyeing /1 hour | 1 | 1 | 1 |
| 10 | Fibres according to Example 4 | Blank dyeing /2 hours | 1 | 2 | 2 |
| 11 | Fibres accor- | Dyeing test /1 hour | 1 | 1 | 1 |

TABLE 6-continued

| No. | Sample | Type of aqueous treatment | Inhibition against mould fungi | | Bacteria |
| | | | Aspergillus fumigatus | Chaetomium globosum | Staph. aureus |
| --- | --- | --- | --- | --- | --- |
| | ding to Example 4 | | | | |
| 12 | Fibres according to Example 4 | Dyeing test /2 hours | 2 | 1–2 | 1–2 |

It may be seen from Table 5 that a steam temperature of at least 120° C. carried out for at least 3 minutes, preferably 5 minutes is necessary for achieving sufficient antimicrobial activity of acrylic fibres which have been spun by the dry spinning process and contain the above-mentioned active ingredients incorporated in the spinning process. Table 6 shows that aqueous boiling treatments, even when carried out at different pH values, do not result in sufficient migration of the active ingredients from the interior of the fibres to the fibre surface. The antimicrobial activity is insufficient in all such cases.

EXAMPLE 5 (COMPARISON)

An acrylonitrile copolymer according to Example 1 was dissolved as indicated there and converted into a spinning solution with a solids content of 30% with the addition of 5% of 1-pyridyl-(2)-4-phenylpyrazolin-5-one. The spinning solution was then filtered and spun by the dry spinning process through a 240 aperture die as indicated in Example 1. The spun material was collected on bobbins, plied and after-treated to form fibres with a final titre of 3.3 dtex without the steaming operation. A proportion of the fibres was again dyed. Both the undyed and the dyed, antimicrobially finished fibres were then spun to form three-cylinder yarns, dtex 228×1 (Nm 36/1) and made up into knitted goods in a Milanese ribbed pattern. The knitted goods were subjected to 10 household washings. Fibres and knitted goods, both dyed and undyed, were then tested microbiologically by the agar diffusion test with the mould fungi and bacteria indicated in Example 1. The grading obtained was in all cases 1, e.g. there was no reduction in the growth of test micro-organisms on the fibres or knitted pieces.

EXAMPLE 6 (COMPARISON)

An acrylonitrile polymer according to Example 1 was dissolved in analogous manner and converted into a spinning solution with a solids content of 30% with the addition of 5% of 1-pyrimidyl-(2)-4-phenylpyrazolin-5-one. The spinning solution was then filtered and spun by the dry spinning process from a 240 aperture die. The spun material was again gathered on bobbins, plied and after-treated to form fibres with a final titre of 3.3 dtex without the steam treatment. A proportion of the fibres was again dyed. Both the undyed and dyed, antimicrobially finished fibres were again made up into knitted goods in a Milanese ribbed pattern. The knitted goods were again subjected to 10 household washings. Fibres and knitted pieces, both dyed and undyed, were then again tested microbiologically by the agar diffusion test, using the mould fungi and bacteria indicated in Example 1. The grading was in all cases 1, i.e. no reduction in the growth of test micro-organisms on the fibres or knitted pieces was observed.

What is claimed is:

1. Threads and fibres of acrylonitrile polymers containing 0.1 to 5% by weight, based on the acrylonitrile polymer, of a compound corresponding to the formula

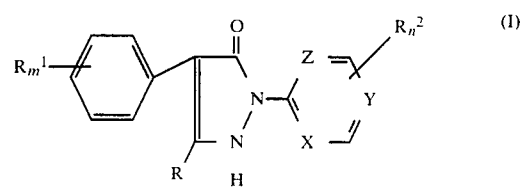

wherein
R represents hydrogen or alkyl,
$R^1$ represents halogen, hydroxyl, unsubstituted or substituted alkyl, unsubstituted or substituted alkoxy, unsubstituted or substituted phenoxy, a group —$S(O)_p$—alkyl which is unsubstituted or substituted in the alkyl portion, nitro, unsubstituted or substituted amino or a condensed carbocyclic or heterocyclic group,
P represents the integer 0, 1 or 2,
$R^2$ represents halogen, an unsubstituted or substituted alkyl group, alkoxy, alkylmercapto, nitro, cyano, aminocarbonyl or a condensed carbocyclic group,
m represents an integer from 0 to 5,
n represents an integer from 0 to 4, and the substituents $R^1$ and $R^2$ may be identical or different when m and/or n represent a number greater than 1, and
X, Y and Z are identical or different and represent a nitrogen atom or the group =CH— or $$=\underset{\underset{R^2}{|}}{C}-,$$

where $R^2$ has the meaning indicated above, with the proviso that at least one of the substituents X, Y, Z is a nitrogen atom.

2. Threads and fibres according to claim 1, wherein
R represents hydrogen, methyl or ethyl,
$R^1$ represents fluorine, chlorine, bromine, methyl, ethyl, n-propyl, isopropyl, trifluoromethyl, dichlorofluoromethyl, methoxy, ethoxy, n-propoxy, isopropoxy, trifluoromethoxy, dichlorofluoromethoxy, methylthiomethoxy, ethylthiomethoxy, 1-methylthio-ethoxy, 2-ethylthioethoxy, phenoxymethoxy, phenoxy, methylthio, ethylthio, trifluoromethylthio, dichlorofluoromethylthio, methoxymethylthio, ethoxymethylthio, methylthiomethylthio, methylsulphinyl, ethylsulphinyl, methylsulphonyl, nitro, cyano, amino, methylamino, ethylamino, dimethylamino, diethylamino, a condensed benzene ring or a condensed 5- or 6-membered heterocyclic ring which has one or two oxygen atoms or a condensed benzene ring or a condensed heterocyclic ring which has one or two oxygen atoms substituted with one or more fluorine atoms, $R^2$ represents fluorine, chlorine, bromine, methyl, ethyl, n-propyl, isopropyl, tert.-butyl, trifluoromethyl, dichlorofluoromethyl, methoxymethyl, ethoxymethyl, methylthiomethyl, methoxy, ethoxy, n-propoxy, isopropoxy, methylthio, ethylthio, nitro, cyano, aminocarbonyl or a condensed benzene ring, m represents an integer from 0 to 3, n represents an integer from 0 to 3 and the substituents $R^1$ and $R^2$ may be identical or different when m and/or n has a value greater than 1, and X, Y and Z are identical or different and represent a nitrogen atom or the group =CH— or

$R^2$ having the meaning indicated above, with the proviso that one or two of the groups X, Y, Z denote a nitrogen atom.

3. Threads and fibres according to claim 1, wherein

R represents hydrogen, methyl or ethyl, $R^1$ represents fluorine, chlorine, bromine, methyl, ethyl, trifluoromethyl, methoxy, ethoxy, trifluoromethoxy, phenoxy, methylthio, ethylthio, trifluoromethylthio, nitro, cyano, amino, dimethylamino, a condensed benzene ring or a condensed 5-membered heterocyclic ring which has two oxygen atoms or a condensed benzene ring or a condensed heterocyclic ring which has two oxygen atoms and is substituted several times with fluorine atoms, $R^2$ represents fluorine, chlorine, bromine, methyl, ethyl, tert.-butyl, trifluoromethyl, methoxy, methylthio, nitro, aminocarbonyl or a condensed benzene ring, m represents an integer from 0 to 3, n represents an integer from 0 to 3, and either X represents a nitrogen atom and Y and Z represent the group =CH— or

or

Y represents a nitrogen atom and

X and Z represent the group =CH— or

or

X and Z each represent a nitrogen atom and

Y represents the group =CH— or

or

X and Y each represent a nitrogen atom and

Z represents the group =CH— or

4. Threads and fibres according to claim 1, containing a compound corresponding to the formula

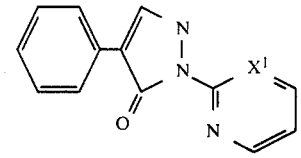

wherein $X^1$ represents N or CH.

5. Threads and fibres according to claim 1, containing from 0.5 to 1% by weight, based on the polymer solids content, of compounds corresponding to formula I.

6. Threads and fibres according to claim 1 of acrylonitrile polymers containing at least 45% by weight of acrylonitrile units.

7. Threads and fibres according to claim 1 of acrylonitrile polymers containing at least 85% by weight of acrylonitrile units.

8. Process for the production of antimicrobially active threads and fibres according to claim 1 by introducing one or more compounds corresponding to formula I in a quantity of from 0.1 to 5% by weight, based on the acrylonitrile polymer, into a polyacrylonitrile spinning solution, and spinning the solution to form threads by the dry spinning process, and subsequently after-treating the threads by washing, stretching, dressing, drying, crimping and cutting them up to fibres, characterized in that the threads and fibres are finally subjected to a process of fixing with saturated steam at a temperature of at least 120° C. for at least 3 minutes.

9. Process according to claim 8, characterized in that fixing is carried out for 3 to 15 minutes at 120° to 150° C.

* * * * *